US012595514B2

(12) United States Patent
Hashimoto et al.

(10) Patent No.: US 12,595,514 B2
(45) Date of Patent: Apr. 7, 2026

(54) ANALYTICAL METHOD AND KIT

(71) Applicant: KABUSHIKI KAISHA TOSHIBA, Tokyo (JP)

(72) Inventors: Koji Hashimoto, Atsugi (JP); Mika Inada, Ota (JP); Keiko Ito, Kawasaki (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 898 days.

(21) Appl. No.: 17/188,101

(22) Filed: Mar. 1, 2021

(65) Prior Publication Data

US 2021/0214804 A1     Jul. 15, 2021

Related U.S. Application Data

(63) Continuation of application No. PCT/JP2019/030606, filed on Aug. 2, 2019.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
CPC ............ C12Q 1/6886; C12Q 2600/158; C12Q 2600/178
See application file for complete search history.

(56) References Cited

U.S. PATENT DOCUMENTS

| | | |
|---|---|---|
| 2012/0315640 A1 | 12/2012 | Tahara |
| 2014/0256562 A1 | 9/2014 | Umansky et al. |
| 2014/0308370 A1 | 10/2014 | Frendewey et al. |
| 2015/0031574 A1 | 1/2015 | Murakami et al. |
| 2017/0016067 A1 | 1/2017 | Cotter et al. |
| 2017/0051359 A1 | 2/2017 | Pegtel et al. |
| 2017/0073764 A1* | 3/2017 | Tahara ................. C12Q 1/6886 |
| 2017/0107581 A1 | 4/2017 | Kawauchi et al. |
| 2017/0130275 A1 | 5/2017 | Kondou et al. |
| 2017/0130278 A1 | 5/2017 | Sudo et al. |
| 2017/0233822 A1 | 8/2017 | Too et al. |
| 2018/0274022 A1 | 9/2018 | Inada et al. |
| 2019/0127793 A1 | 5/2019 | Ito et al. |
| 2019/0285567 A1 | 9/2019 | Hashimoto et al. |
| 2020/0115758 A1 | 4/2020 | Kawauchi et al. |

FOREIGN PATENT DOCUMENTS

| | | |
|---|---|---|
| CN | 101555520 A | 10/2009 |
| CN | 108103198 A | 6/2018 |
| JP | 2013-198483 A | 10/2013 |
| JP | 2014-64570 A | 4/2014 |
| JP | 2014-511709 A | 5/2014 |
| JP | 2016-518124 A | 6/2016 |
| JP | 2017-509333 A | 4/2017 |
| JP | 2017-514519 A | 6/2017 |
| JP | 2017-525350 A | 9/2017 |
| JP | 2018-27089 A | 2/2018 |
| JP | 2018-153157 A | 10/2018 |
| JP | 2019-17383 A | 2/2019 |
| JP | 2019-154318 A | 9/2019 |
| WO | WO-2009136693 A1 * | 11/2009 | .......... C12Q 1/6876 |
| WO | WO 2011/078037 A1 | 6/2011 |
| WO | WO 2013/125691 A1 | 8/2013 |
| WO | WO 2014/192907 A | 12/2014 |
| WO | WO 2014/200065 A1 | 12/2014 |
| WO | WO 2015/133477 A1 | 9/2015 |
| WO | WO 2015/190542 A1 | 12/2015 |
| WO | WO 2015/190591 A1 | 12/2015 |
| WO | WO 2015/194610 A1 | 12/2015 |
| WO | WO 2017/171048 A1 | 10/2017 |

OTHER PUBLICATIONS

Zhou et al., Plasma miRNAs in diagnosis and prognosis of pancreatic cancer: A miRNA expression analysis. Gene. Oct. 5, 2018;673:181-193. doi: 10.1016/j.gene.2018.06.037. Epub Jun. 18, 2018. PMID: 29913239; cited as Other References #BZ, on IDS filed Mar. 1, 2021 (Year: 2018).*

Finotti et al. Liquid biopsy and PCR-free ultrasensitive detection systems in oncology (Review). Int J Oncol. Oct. 2018;53(4):1395-1434. doi: 10.3892/ijo.2018.4516. Epub Aug. 6, 2018. PMID: 30085333; PMCID: PMC6086621. (Year: 2018).*

Cancer Stat Facts: Common Cancer Sites; NIH, Archived Aug. 11, 2018 on WaybackMachine (Year: 2018).*

Cancer Stat Facts: Common Cancer Sites; Archived Aug. 11, 2018 on WaybackMachine (Year: 2018).*

Zhou et al., Plasma miRNAs in diagnosis and prognosis of pancreatic cancer: A miRNA expression analysis. Gene. Oct. 5, 2018;673:181-193. doi: 10.1016/j.gene.2018.06.037. Epub Jun. 18, 2018. PMID: 29913239 (Year: 2018).*

Treder, Krzysztof, et al. "Detection of potato virus Y (PVY) by reverse-transcription loop-mediated nucleic acid amplification (RT-LAMP)." Plant Breeding and Seed Science 75 (2017): 77-85. (Year: 2017).*

NIH—Cancer Stat Facts: Common Cancer Sites; Archived Aug. 11, 2018 on WaybackMachine (Year: 2018).*

"miRCURY LNA™ Universal RT microRNA PCR system," Cosmo Bio Co., Ltd., Feb. 1, 2012, (with English translation), 20 pages.

Zhou, X. et al., "Plasma miRNAs in diagnosis and prognosis of pancreatic cancer: A miRNA expression analysis," Gene, vol. 673, 2018, 53 pages.

* cited by examiner

*Primary Examiner* — Aaron A Priest
*Assistant Examiner* — Tian N Yu
(74) *Attorney, Agent, or Firm* — Oblon, McClelland, Maier & Neustadt, L.L.P.

(57) ABSTRACT

In general, according to one embodiment, analytical method for determining the presence/absence of the contraction of the pancreatic cancer in subjects is provided. The method comprises quantifying hsa-miR-122-5p in a sample originated from a subject.

8 Claims, 6 Drawing Sheets

Specification includes a Sequence Listing.

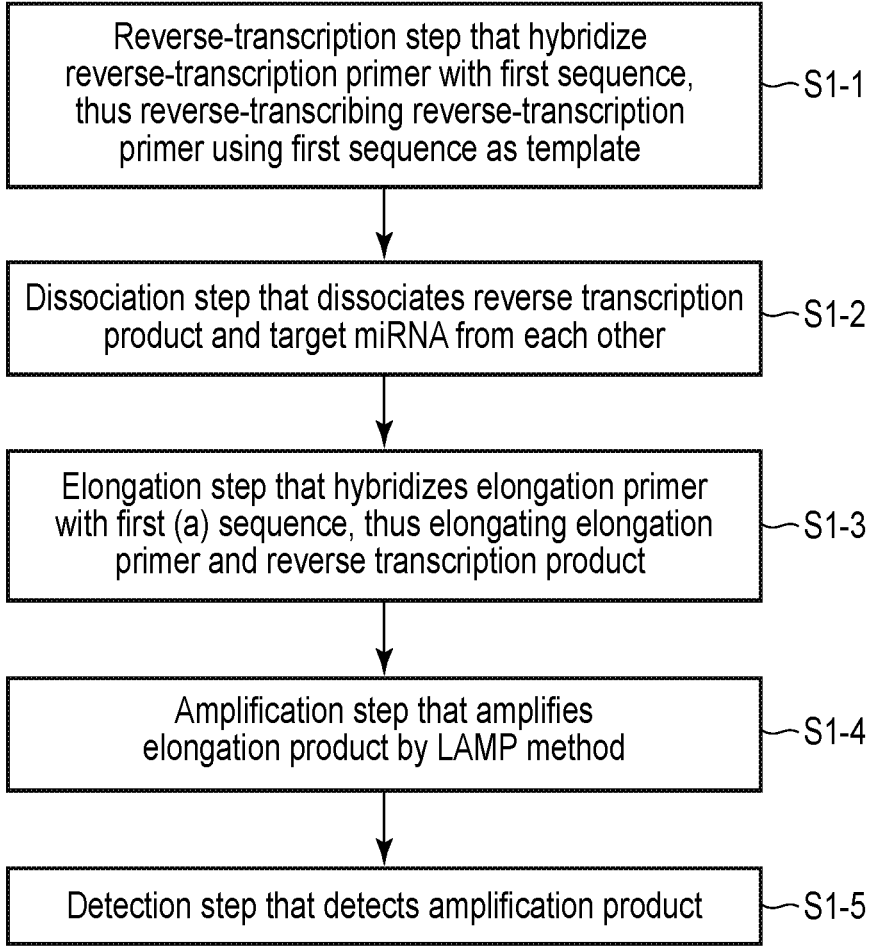

Quantification step that quantify hsa-miR-122-5p
in sample originated from subject — S1

F I G. 1

Reverse-transcription step that hybridize
reverse-transcription primer with first sequence,
thus reverse-transcribing reverse-transcription
primer using first sequence as template — S1-1

Dissociation step that dissociates reverse transcription
product and target miRNA from each other — S1-2

Elongation step that hybridizes elongation primer
with first (a) sequence, thus elongating elongation
primer and reverse transcription product — S1-3

Amplification step that amplifies
elongation product by LAMP method — S1-4

Detection step that detects amplification product — S1-5

F I G. 2

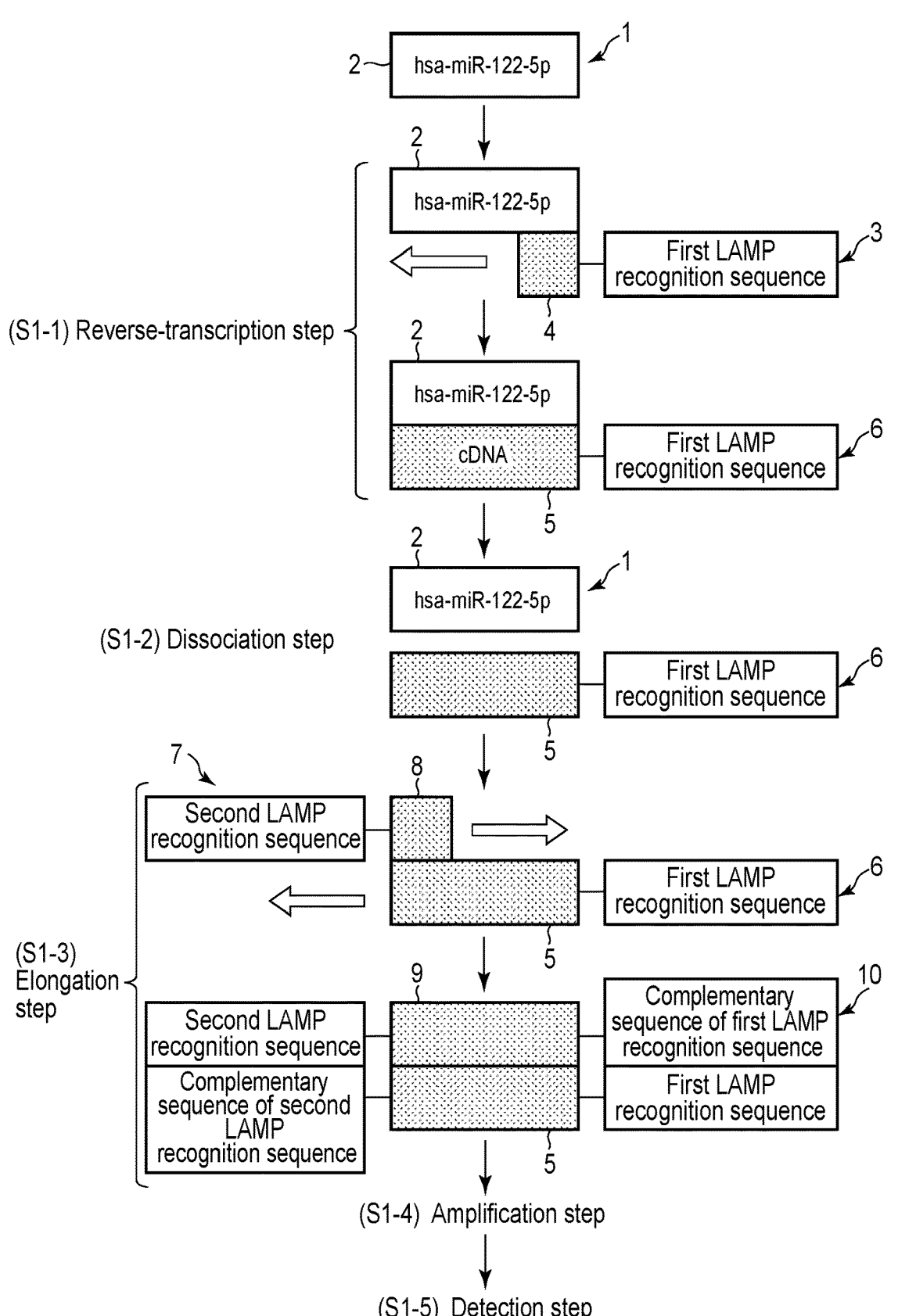
F I G. 3

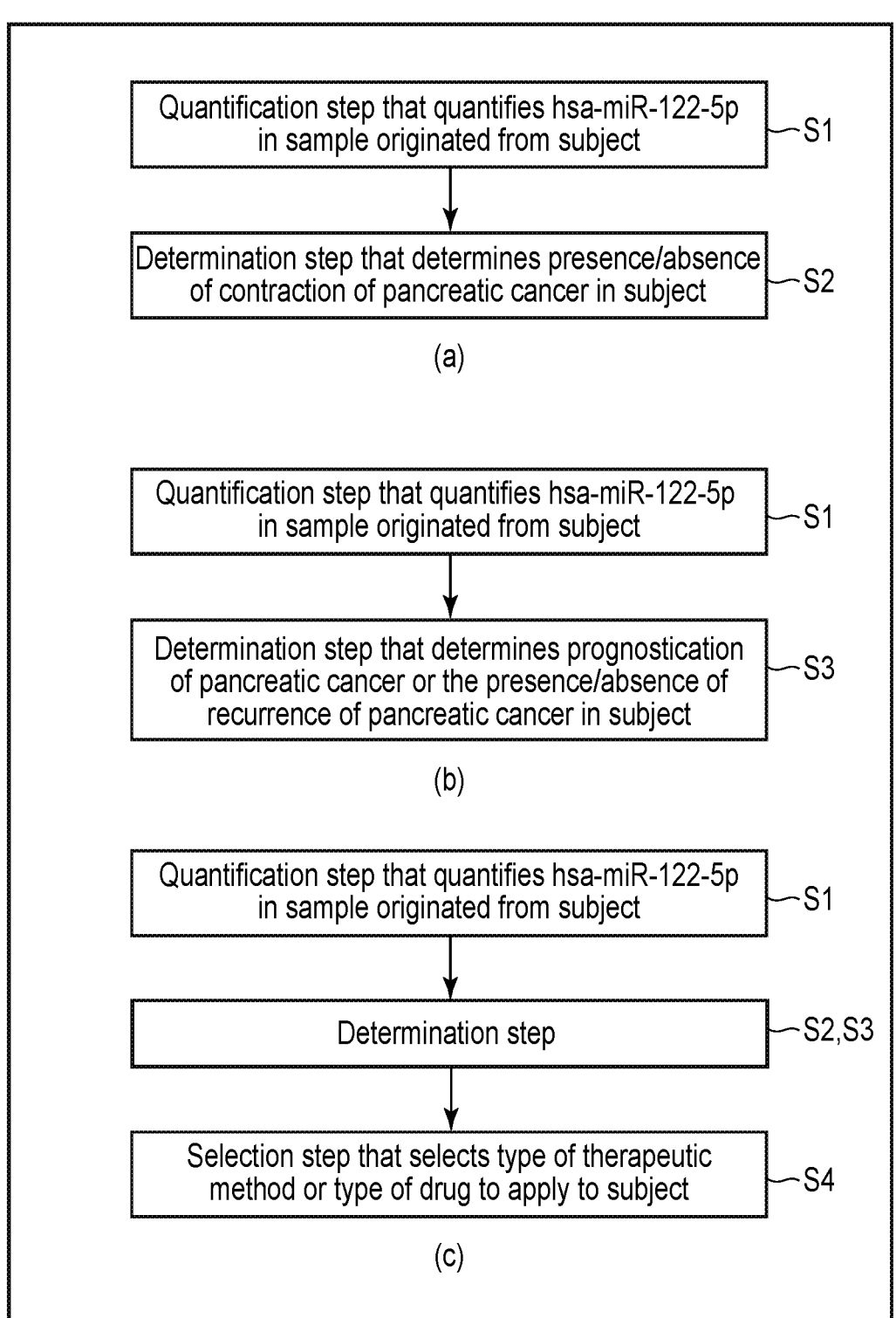
F I G. 4

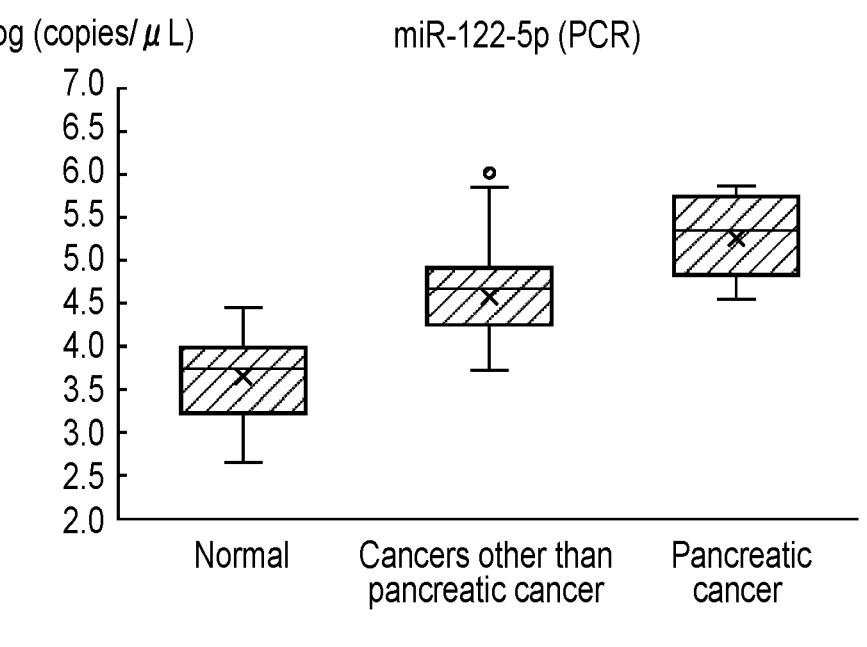
log (copies/$\mu$L)                miR-122-5p (PCR)
F I G. 6
F I G. 7

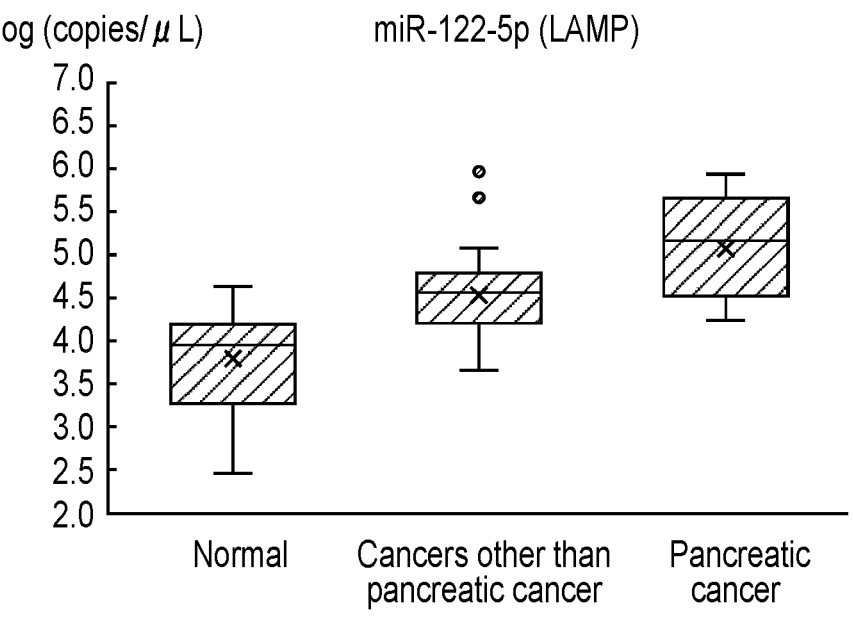
F I G. 8
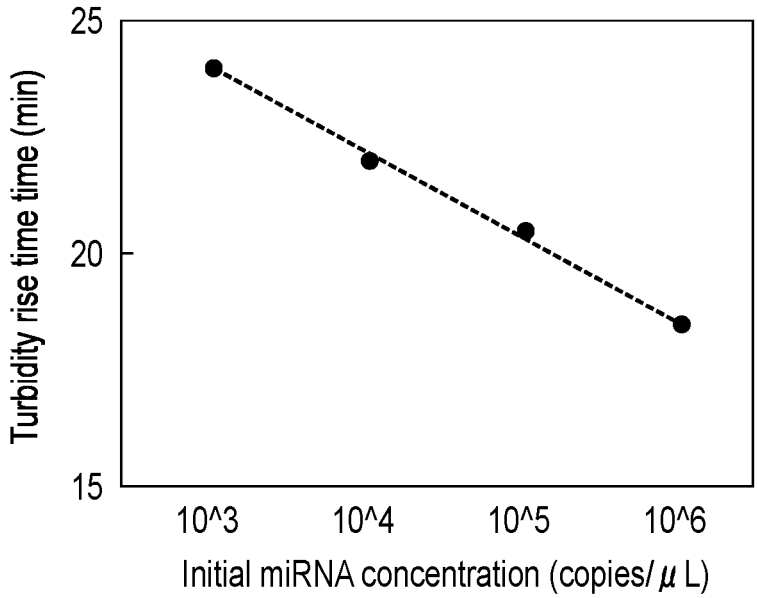
F I G. 9

SEQUENCE LISTING

```
<160> NUMBER OF SEQ ID NOS: 11

<210> SEQ ID NO 1
<211> LENGTH: 22
<212> TYPE: RNA
<213> ORGANISM: human

<400> SEQUENCE: 1
uggaguguga caaugguguu ug                                    22

<210> SEQ ID NO 2
<211> LENGTH: 28
<212> TYPE: DNA
<213> ORGANISM: artificial
<220> FEATURE:
<223> OTHER INFORMATION: RT primer

<400> SEQUENCE: 2
cggaacggca taaaaagccc aaacacca                              28

<210> SEQ ID NO 3
<211> LENGTH: 77
<212> TYPE: DNA
<213> ORGANISM: artificial
<220> FEATURE:
<223> OTHER INFORMATION: EL primer

<400> SEQUENCE: 3
gaatgtgacc acgcggatac agactttcga tccacgctgg gaccgaggcc agactctacc      60
tgggtggagt gtgacaa                                          77

<210> SEQ ID NO 4
<211> LENGTH: 29
<212> TYPE: DNA
<213> ORGANISM: artificial
<220> FEATURE:
<223> OTHER INFORMATION: RT primer

<400> SEQUENCE: 4
ggcgccgaaa caatattcct caaacacca                             29

<210> SEQ ID NO 5
<211> LENGTH: 76
<212> TYPE: DNA
<213> ORGANISM: artificial
<220> FEATURE:
<223> OTHER INFORMATION: EL primer

<400> SEQUENCE: 5
gatctagaag gccgccagtc gttcagccta cggccgttgt catccgtagc aggacgctca      60
```

-continued

```
gggtggagtg tgacaa                                                 76

<210> SEQ ID NO 6
<211> LENGTH: 40
<212> TYPE: DNA
<213> ORGANISM: artificial
<220> FEATURE:
<223> OTHER INFORMATION: FIP primer

<400> SEQUENCE: 6
ccagcgtgga tcgaaagtct gtgaatgtga ccacgcggat                       40

<210> SEQ ID NO 7
<211> LENGTH: 40
<212> TYPE: DNA
<213> ORGANISM: artificial
<220> FEATURE:
<223> OTHER INFORMATION: BIP primer

<400> SEQUENCE: 7
gaccgaggcc agactctacc tcggaacggc ataaaaagcc                       40

<210> SEQ ID NO 8
<211> LENGTH: 18
<212> TYPE: DNA
<213> ORGANISM: artificial
<220> FEATURE:
<223> OTHER INFORMATION: LB primer

<400> SEQUENCE: 8
gtgtgacaat ggtgtttg                                               18

<210> SEQ ID NO 9
<211> LENGTH: 18
<212> TYPE: DNA
<213> ORGANISM: artificial
<220> FEATURE:
<223> OTHER INFORMATION: LB primer

<400> SEQUENCE: 9
tgacaatggt gtttgggc                                               18

<210> SEQ ID NO 10
<211> LENGTH: 38
<212> TYPE: DNA
<213> ORGANISM: artificial
<220> FEATURE:
<223> OTHER INFORMATION: FIP primer

<400> SEQUENCE: 10
aacggccgta ggctgaacgg atctagaagg ccgccagt                         38

<210> SEQ ID NO 11
<211> LENGTH: 42
<212> TYPE: DNA
<213> ORGANISM: artificial
<220> FEATURE:
<223> OTHER INFORMATION: BIP primer

<400> SEQUENCE: 11
gtcatccgta gcaggacgct caggcgccga acaatattc ct                     42
```

ANALYTICAL METHOD AND KIT

CROSS-REFERENCE TO RELATED APPLICATIONS

This application is a Continuation Application of PCT Application No. PCT/JP2019/030606, filed Aug. 2, 2019, the entire contents of which are incorporated herein by reference.

FIELD

Embodiments described herein relate generally to an analytical method and a kit.

BACKGROUND

Recently, the relationship between microRNA (miRNA) and diseases is getting attention. The miRNA has a function to regulate a gene expression, and it is reported that the type and the amount of expression thereof change from an early stage in various kinds of diseases. That is, in a patient with a certain disease, the quantity of a particular miRNA increases or decreases as compared to the case of a normal persons. Therefore, examination of the quantity of the miRNA in a sample collected from a subject can be measures to know whether the subject patient contracts the certain disease.

BRIEF DESCRIPTION OF THE DRAWINGS

FIG. 1 shows a flowchart of an example of the analytical method of the first embodiment.

FIG. 2 shows a flowchart of an example of the quantification process of the embodiment.

FIG. 3 shows a schematic diagram of an example of the quantification process of the embodiment.

FIG. 4 shows a flowchart of an example of the analytical method of the first embodiment.

FIG. 6 shows a graph of experimental results in example 1.

FIG. 7 shows a graph of experimental results in example 2.

FIG. 8 shows a graph of experimental results in example 3.

FIG. 9 shows a graph of experimental results in example 4.

DETAILED DESCRIPTION

Figure 5:
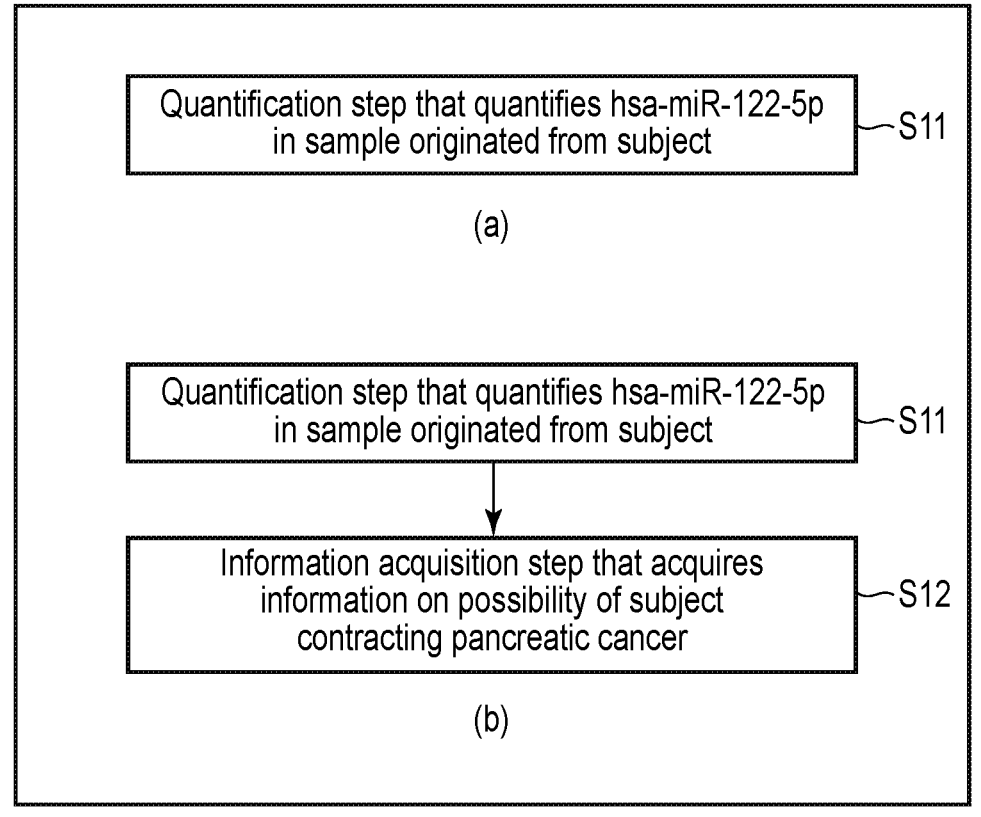
FIG. 5 shows a flowchart of an example of the analytical method of the second embodiment.

In general, according to one embodiment, analytical method for determining the presence/absence of the contraction of the pancreatic cancer in subjects is provided. The method comprises quantifying hsa-miR-122-5p in a sample originated from a subject.

Analytical method and kits of the embodiments will be described below with reference to the accompanying drawings.

First Embodiment (Analytical Method)

The analytical method of the embodiment is a method for determining the presence/absence of contraction of pancreatic cancer in a subject.

The subject may be an animal to be subjected to the analysis, which is an animal providing a sample which will be described below. The subject may be an animal contracting some kind of diseases or may be a normal animal. For example, the subject may be an animal which may be contracting pancreatic cancer, an animal which may have been contracted pancreatic cancer or the like.

The subject may preferably be a human, or the subject may be some other animal. Some other animal may be, for example, a mammal, such as a primate such as a monkey, a rodent such as a mouse, rat or guinea pig, a companion animal such as dog, cat or rabbit, or a domestic animal such as horse, cow or pigs, or a displayed animal or the like.

The pancreatic cancer according to the embodiment refers to a malignant tumor (neoplasm) that begins to develop in pancreas. The pancreatic cancer includes those generally referred to as "pancreas cancer", "pancreatic tumor" or "cancer of pancreas". Further, the pancreatic cancer according to the embodiment includes any types of pancreatic cancer, for example, an epithelial tumor (for example, internal secretion tumor and external secretion tumor) and also a non-epithelial tumor. Furthermore, the pancreatic cancer includes that of any stage of the disease, that is, for example, a state that a cancer remains within pancreas, a state that the cancer reaches the surrounding tissues, a state that the cancer metastasizes in lymph node, a state that the cancer metastasizes to a farther remote organ, and the like.

The analytical method comprises quantifying hsa-miR-122-5p in a sample originated from a subject (quantification step (S1)), as shown in FIG. 1.

A sample originated from the may preferably be serum. The sample may be some other body fluid, for example, blood, plasma, stroma liquid, urine, feces, sweat, saliva, oral mucosa, intranasal mucous membrane, pharyngeal mucosa, sputum, lymph fluid, cerebrospinal fluid, tears, mother's milk, amniotic fluid, semen or the like. Or, the sample may be cultured tissues or cells sampled from a subject, or a supernatant thereof. Or it may be an established cell line from the cultured cells.

The method of collecting a sample may be a general method based on the type of the sample. The collected sample may be, for example, pre-treated with any well-known means so as to set it, for example, to be in a condition not to inhibit a reverse transcription, elongation and amplification reactions, which will be described below or to set it in a condition more suitable for these reactions. The pre-treatment is, for example, slicing, homogenizing, centrifuging, precipitation, extraction and/or separation or the like.

For example, the extraction may be carried out with use of a commercially available nucleic acid extraction kit. Or, the extraction may be carried out without using a commercially available kit, but by, for example, diluting the material with a buffer solution, subjecting it to a heat-treatment at 80 to 100° C. and centrifuging, and then collecting its supernatant.

The hsa-miR-122-5p is a miRNA having the following sequence:

UGGAGUGUGACAAUGGUGUUUG (SEQ ID NO. 1).

Note that the hsa-miR-122-5p may as well be referred to as "target miRNA" hereinafter. Further, the sequence of SEQ ID NO. 1 may as well be referred to as "the first sequence".

The quantification of a target miRNA can be carried out by a general method that can quantify RNA. For example, a PCR method, a qPCR method, a LAMP method or the like, a turbidity or an absorbency measurement method, a fluorometry, or an electrochemical measurement method or a combination of any of these, or the like can be used.

When using the qPCR method, for example, a commercially available kit can be used for quantification. Examples of the commercially available kit is TaqMan (registered trademark) Advanced miRNA Assays (a product of ThermoFischer, ID: 477827 mir), miRCURY LNA miRNAPCR Assays (a product in Kia Gene, Catalog No. YP02103132) and the like. Further, quantification can be carried out by using SYBR (registered trademark) Green qPCR microRNA detection system (a product of Origin Technologies) and a primer which specifically amplifies a target miRNA.

A preferable quantification step (S1) is a method carried out by specifically reverse-transcribing and elongating a target miRNA, amplifying the elongated product by the LAMP method, and detecting the amplified product. An example of such a quantification step (S1) will be described as follows. The quantification step (S1) includes the following steps shown in, for example, FIGS. 2 and 3.

(S1-1) a reverse-transcription step containing:

hybridizing a first primer portion 4 included in a reverse-transcription primer 3 (to be referred to also as "RT primer" hereinafter) and a first sequence 2 of the target miRNA1, wherein the first primer portion 4 is hybridizable with the first sequence 2, and a reverse-transcription primer 3 further contains a first LAMP recognition sequence, reverse-transcribing the first sequence 2, and obtaining a reverse transcription product 6 containing a first (a) sequence 5 (complementary DNA of a target miRNA1);

(S1-2) a dissociation step containing dissociating the reverse transcription product 6 and the target miRNA1 from each other;

(S1-3) an elongation step containing:

hybridizing a second primer portion 8 included in an elongation primer 7 (to be referred to also as "RT primer" hereinafter) and the first (a) sequence 5 included in the reverse transcription product 6, wherein the second primer portion 8 is hybridizable with the first (a) sequence 5, and the elongation primer 7 further contains the second LAMP recognition sequence, elongating the EL primer 7 and the reverse transcription product 6 using these as templates with respect to each other, and obtaining an elongation product 10 containing a complementary sequence 9 of the first (a) sequence 5 (that is, a DNA sequence corresponding to the first sequence); and (S1-4) an amplification step containing amplifying the elongation product 10 by the LAMP reaction, and obtaining an amplification product; and (S1-5) a detection step containing detecting the obtained amplification product.

The first primer portion 4 of the RT primer 3 is a nucleic acid sequence which hybridizes with the first sequence 2 and acts as a primer which reverse-transcribe the first sequence 2 to generate complementary DNA (cDNA), which is the first (a) sequence 5. The first primer portion 4 comprises, for example, at least five continuous base sequence containing a 3' end of the first sequence 2.

The second primer portion 8 of the EL primer 7 is a nucleic acid sequence which hybridizes with the first (a) sequence 5 and acts as a primer for generate a complementary sequence thereof, which is sequence 9. The second primer portion 8 comprises, for example, at least five continuous base sequence containing the 3' end of the first (a) sequence 5.

The first primer portion 4 and the second primer portion 8 may be constituted by only DNA or may contain LNA and/or PNA. The more amounts of these contained, the stronger the bonding strength of the hybridization can be obtained. Therefore, the number of LNAs and/or PNAs may be determined according to desired Tm value with respect to the sequence to be hybridized. For example, when LNA and/or PNA are contained, the reverse transcription step (S1-1) and the elongation step (S1-3) can be carried out at higher temperature, and thus nonspecific bonds can be inhibited. As a result, the target miRNA can be reverse-transcribed and elongated with higher accuracy.

The first LAMP recognition sequence and the second LAMP recognition sequence are nucleic acid base sequences containing a sequence to which a LAMP primer is bonded (that is, recognition sequence) in the amplification step (S1-4). The recognition sequence may be generally that used in the LAMP primer. For example, the first LAMP recognition sequence may contain a B1 sequence, a B2 sequence (and optionally an LB sequence) and a B1 sequence in the order from a first primer portion 4 side towards the 5' end. The second LAMP recognition sequence may contain an F1 sequence, an F2 sequence (and optionally an LF sequence) and an F1 sequence in the order from the second primer portion 8 side towards the 5' end.

However, it is preferable that the first LAMP recognition sequence and the second LAMP recognition sequence contain recognition sequences in combination of the following (1) to (7). Here, the order of each recognition sequence listed below is that from the first primer portion 4 or second primer portion 8 side towards the 5' end. The symbol "c" means a complementary sequence of the sequence described just before that. For example, the "LBc sequence" means a complementary sequence of the LB sequence. A "dummy sequence" is a nucleic acid sequence containing a base sequence different from a first (a) sequence, an F2 sequence, an F1 sequence, an LF sequence, a B1 sequence, a B2 sequence, an LB sequence and the complementary sequence thereof.

(1) The first LAMP recognition sequence contains a B2 sequence, and the second LAMP recognition sequence contains a B1c sequence, an F1 sequence and an F2 sequence. (In this case, at least a part of the complementary sequence of the first (a) sequence (sequence 9) is defined as an LB sequence.)

(2) The first LAMP recognition sequence contains an LBc sequence and a B2 sequence, and the second LAMP recognition sequence contains a B1c sequence, an F1 sequence and an F2 sequence.

(3) The first LAMP recognition sequence contains a dummy sequence and a B2 sequence, and the second LAMP recognition sequence contains B1c sequence, F1 sequence and F2 sequence.

(4) The first LAMP recognition sequence contains a B1 sequence and a B2 sequence, and the second LAMP recognition sequence contains an F1 sequence, an LFc sequence and an F2 sequence.

(5) The first LAMP recognition sequence contains a B2 sequence, and the second LAMP recognition sequence contains an F1 sequence, an LFc sequence and an F2 sequence.

(6) The first LAMP recognition sequence contains an LBc sequence and a B2 sequence, and the second LAMP recognition sequence contains an F1 sequence and an F2 sequence.

(7) The first LAMP recognition sequence contains a B1 sequence and a B2 sequence, and the second LAMP recognition sequence contains an LFc sequence and an F2 sequence.

With the combinations listed above, the target miRNA can be more specifically reverse-transcribed and elongated, and thus the accuracy of detection of pancreatic cancer can be improved.

When the combination of the LAMP recognition sequences is selected as (1) above, it is preferable to use a reverse transcription and elongation primer set A or B, which contains an RT primer 3 and an EL primer 7 listed in Table 1 below.

TABLE 1

|  | Reverse transcription and elongation primer set A | |
|---|---|---|
| Primer | SEQ ID NO | Sequence (5'-3') |
| RT | 2 | CGGAACGGCATAAAAAGCCCAAACACCA |
| EL | 3 | GAATGTGACCACGCGGATACAGACTTTCGATCCACGCTGGGACCGAG GCCAGACTCTACCTGGGTGGAGTGTGACAA |
|  | Reverse transcription and elongation primer set B | |
| Primer | SEQ ID NO | Sequence (5'-3') |
| RT | 4 | GGCGCCGAAACAATATTCCTCAAACACCA |
| EL | 5 | GATCTAGAAGGCCGCCAGTCGTTCAGCCTACGGCCGTTGTCATCCGTAG CAGGACGCTCAGGGTGGAGTGTGACAA |

*Bold letters indicate first primer or second primer

A spacer sequence may exist between the first primer portion 4 and the first LAMP recognition sequence of the RT primer 3, between the second primer portion 8 and the second LAMP recognition sequence of the EL primer 7 and/or between a respective pair of recognition sequences contained in each LAMP recognition sequence. The spacer sequence is a nucleic acid sequence different from the first (a) sequence, each recognition sequence and complementary sequences thereof, which does not adversely affect the amplification reaction of the elongation product, which will be described below. The spacer sequence may be constituted by only DNA or may contain LNA and/or PNA. For example, the spacer sequence is of 1 base to 16 bases, and it is preferable that it may be a poly-T sequence, a poly-A sequence or the like.

The reverse transcription production step (S1-1) is carried out, for example, by adding the RT primer 3, reverse transcriptase, salt and substrates such as deoxynucleoside triphosphate (dNTP) and the like (as needed, a thickener, pH-adjustment buffer material, a surfactant as reaction reagents, ions which enhance annealing specificity and/or ions serving as a cofactor of reverse transcriptase) and the like, to the sample. Usable examples of reverse transcriptase are M-MuLV reverse transcriptase, AMV reverse transcriptase, transcripter reverse transcriptase, SuperScript (registered trademark) transcripter reverse transcriptase and MultiScribe reverse transcriptase. It is preferable to maintain the temperature at, for example, approximately 10° C. to 55° C.

The dissociation step (S1-2) can be carried out by, for example, heating the reaction solution to 80° C. to 100° C.

The elongation step (S1-3) is carried out by, for example, adding the EL primer 7, DNA polymerase, salt and substrates such as dNTP and the like (as needed, a thickener, pH-adjustment buffer material, a surfactant and ions) and the like to a solution containing the reverse transcription product 6. It is preferable to maintain the temperature at approximately 10° C. to 80° C.

The amplification step (S1-4) is carried out using the LAMP method. This step includes adding a LAMP primer set, strand-displaced DNA polymerase, salt and substrates such as dNTP (as needed, a thickener, pH-adjustment buffer, a surfactant and ions) and the like, to a solution containing an elongation product 10, and maintaining the solution under conditions of an isothermal amplification reaction.

The type and the sequence of the LAMP primer set are selected according to the sequences of the first LAMP recognition sequence and the second LAMP recognition sequence. For example, the LAMP primer set contains an FIP primer and a BIP primer, correspond to the sequences of the first LAMP recognition sequence and the second LAMP recognition sequence. If necessary, an F3 primer, a B3 primer and/or a loop primer such as LF primer or an LB primer or the like may be contained.

When the combination of the LAMP recognition sequences is selected as (1) above, for example, a LAMP primer set A or B listed in Table 2 below can be used as the LAMP primer set. Note that, for the LB primer of the LAMP primer set A, one of SEQ ID NOS. 8 and 9 can be used.

TABLE 2

|  | LAMP primer set A | |
|---|---|---|
| Primer | SEQ ID NO | Sequence (5'-3') |
| FIP | 6 | CCAGCGTGGATCGAAAGTCTGTGAATGTGACCACGCGGAT |
| BIP | 7 | GACCGAGGCCAGACTCTACCTCGGAACGGCATAAAAAGCC |

TABLE 2-continued

| LB | 8 | GTGTGACAATGGTGTTTG |
|----|---|---------------------|
| LB | 9 | TGACAATGGTGTTTGGGC |

LAMP primer set B

| Primer | SEQ ID NO | Sequence (5'-3') |
|--------|-----------|-------------------|
| FIP | 10 | AACGGCCGTAGGCTGAACGGATCTAGAAGGCCGCCAGT |
| BIP | 11 | GTCATCCGTAGCAGGACGCTCAGGCGCCGAAACAATATTCCT |
| LB | 8 | GTGTGACAATGGTGTTTG |

According to the above-discussed steps, the target miRNA can be more specifically reverse-transcribed, elongated and amplified. Particularly, in the case of using the primers shown in Tables 1 and 2, the specificity in the reverse transcription, elongation and amplification improves. Therefore, it is possible to detect the presence/absence of contraction of pancreatic cancer at higher sensitivity.

The detection step (S1-5) can be carried out by a general method for detecting nucleic acid. For example, a signal of the turbidity, an optical signal or an electrochemical signal and the like can be used for the detection step.

When using the turbidity, for example, the turbidity of the reaction solution, which increases depending on the presence of the amplification product or the amplification reaction, or the amount of change in turbidity or the rise time of the turbidity are detected. The detection can be carried out by, for example, using a turbidimeter or a spectrophotometer or visual inspection or the like.

When using the optical signal, for example, the amplification reaction may be carried out in the presence of a labeling substance (a fluorescent reagent, intercalator or the like) which produces an optical signal which changes according to the presence of the amplification product or the amplification reaction, and the amount, the amount of change or the rise time of the optical signal may be detected. The detection can be carried out by, for example, using one of the well-known optical sensors, or visual inspection or the like.

When using the electrochemical signal, the amplification reaction may be carried out in the presence of a labeling substance (a redox probe or the like) which produces the electrochemical signal which changes according to the increase in the amplification product, and the amount, the amount of change or the rise time of the electrochemical signal may be detected. The detection can be carried out by, for example, using am electrochemical detection device with an electrode.

The electrochemical detection device includes, for example, a chip. The chip comprises a substrate comprising an electrode on one surface. The electrode may preferably be, for example, gold because of its high sensitivity. When a solution containing the amplification product is brought in on the one surface, the electrode is brought into contact with the solution, and thus an electrochemical signal can be detected from the labeling substance present there.

Above described detections of the turbidity, optical signal and electrochemical signal and the like may be carried out at a particular time point after the initiation of the amplification reaction, or may be carried out over time. The detection over time may mean continuous detection or detection at a plurality of time points with predetermined time intervals.

Further, for the detection of the amplification product, for example, a nucleic acid probe containing at least a part of the sequence of a target miRNA, cDNA of the target miRNA, the elongation product 11 or a complementary sequence thereof may be used. By detecting the hybridization between such a nucleic acid probe and amplification product, the amplification product can be detected.

As described above, the amount, the amount of change, the rise time of each signal obtained in the detection step (S1-5) reflect the amount of the amplification product. From these data items, the amount of the target miRNA originally present in the sample can be calculated (quantified).

For example, the greater, the amount of the target miRNA present in the sample, the shorter, the time for rising the change in signal can be observed. Therefore, using an analytical curve representing the relationship between the rise time and the amount of target miRNA present, the target miRNA in the sample can be quantified. The analytical curve can be prepared by measuring the rise time of the signal about a plurality of standard samples containing the target miRNA at different known concentrations. The analytical curve is compared with the results of the measurement of the rise time obtained for the sample originated from the subject. Thus, the amount of the target miRNA present in the sample can be calculated.

For example, the amount of a target miRNA present in a sample can be obtained as the number of copies of the target miRNA per unit quantity of the sample.

From the quantification result obtained in the quantification step (S1) according to one of the methods discussed above, the presence/absence of contraction of pancreatic cancer of the subject can be determined. Such determination can be made by, for example, a determination step (S2) that can be carried out after the quantification step (S1) shown in FIG. 4, part (a).

For example, in the determination step (S2), when the amount of the target miRNA present in the subject is greater than the amount of the target miRNA in a control, it can be determined that the subject contracts pancreatic cancer. The control may be a normal body. The normal body means an individual which does not contract at least pancreatic cancer. It is preferable that the normal body be a healthy individual not contracting any diseases or abnormalities.

Here, an individual selected as a control can be an individual different from the subject to be examined by the analytical method, but it is preferable that the individual belong to the same species, that is, if the subject is a human, it may be a human. Further, physical conditions such as the age, sex, height and weight of the control and the number of persons in the control are not particularly limited, but the physical conditions may preferably be the same or similar to those the subject to be examined by the analytical method.

The amount of the target miRNA present in the control can be that obtained using the same or similar kind of sample and method in advance before carrying out the analytical method of the embodiment. Or, the amount of the target miRNA present in the control may be a value obtained from the past findings such as of literatures and the like.

Or, when the quantification value obtained in the quantification step (S1) is higher than or equal to a predetermined threshold value, it can be determined that the subject contracts pancreatic cancer. For example, the threshold value can be decided by comparing the measurements of the target miRNA quantification values of a normal individual or an individual having some other kind of cancer and an individual contracting pancreatic cancer, obtained by the same method as that used in the quantification step (S1), with each other. Each "individual" may contain a plurality of individuals. The threshold value may vary according to the method employed, the type of the sample, and the measurement conditions.

Here, the determination of a subject contracting pancreatic cancer also includes a determination that the subject has a high possibility of contracting pancreatic cancer.

Further, the determination of a subject contracting pancreatic cancer also includes a determining the presence/absence of contraction of pancreatic cancer of the subject as distinct from the other cancers. In other words, when determined to contract pancreatic cancer in the determination step (S2), it can mean that the subject is contracting no other cancers but pancreatic cancer. The other cancers include, for example, those classified as other than the pancreatic cancer (malignant tumor, malignant neoplasm, carcinoma and sarcoma). For example, the other cancers include breast cancer, colon cancer, stomach cancer, lung cancer, ovarian cancer, prostate cancer, bile duct cancer, esophagus cancer, liver cancer, brain tumor, bladder cancer, sarcoma, endometrial cancer and uterus sarcoma and the like.

Further, the determination of a subject contracting pancreatic cancer also includes a determination as to prognosis of the pancreatic cancer or the presence/absence of the recurrence of the pancreatic cancer in the subject. In this case, the subject can be, for example, a subject which have been determined to contract pancreatic cancer before subjected to the analytical method, a subject which has been treated for the pancreatic cancer, a subject which have been healed from pancreatic cancer and/or a subject subjected to a following-up for pancreatic cancer, or the like.

For example, when a result of a quantification of the target miRNA in a subject indicates that the quantification value is higher than that of the control or at a predetermined threshold or higher, it can be determined that the prognosis of pancreatic cancer is poor, or pancreatic cancer recurs or is highly likely to have recur in the subject. Such an analytical method includes a determination step (S3) which determines the prognosis of pancreatic cancer or the presence/absence of the recurrence of the pancreatic cancer in the subject from the result of the quantification after the quantification step (S1) as shown in FIG. 4, part (b).

In another embodiment, after the determination step (S2) or (S3), a type of therapeutic method or a type of drug to apply to a subject can be selected according to the result. The therapeutic method or the drug is for the treatment of pancreatic cancer. The type of therapeutic method or the type of drug includes the therapeutic method, the dosage of the drug, the timing or the period thereof. Such an analytical method includes a selection step (S4) for selecting a type of therapeutic method or a type of drug to apply to a subject based on the result of the quantification after the determination step (S2) or (S3) as shown in FIG. 4, part (c).

Moreover, in another embodiment, in order to make the determination more reliable, after the determination step (S2) or (S3), the subject may be subjected to a further examination for the pancreatic cancer, that is, for example, cytodiagnosis and the like.

The analytical method of the embodiment may not include a step of detecting or quantifying a marker other than hsa-miR-122-5p. Then, the determination of the presence/absence of contraction of pancreatic cancer is carried out without using the results of the detection or quantification of a marker other than hsa-miR-122-5p. That is, according to the analytical method of the embodiment, by quantifying one type of miRNA (hsa-miR-122-5p), the presence/absence of contraction of pancreatic cancer in the subject can be easily determined. The marker other than hsa-miR-122-5p includes miRNA, RNA, DNA, protein, glycoprotein, peptide and the like.

Further, with the analytical method of the embodiment, serum, which can be easily collected by medical examinations and the like, can be used, and therefore pancreatic cancer can be early detected. In addition, the analytical method of the embodiment can greatly reduce the physical and economic burden of the subject as compared to cytodiagnosis and the like, and the procedure is easy for laboratory technicians to perform with less load. Further, with the serum, more accurately examination can be carried out because the concentration of miRNA contained therein is stable.

(Marker)

According to the embodiment, a marker for the detection of pancreatic cancer, which contains hsa-miR-122-5p, is provided.

For example, the marker for the detection of pancreatic cancer of the embodiment can be used for the determination of the presence/absence of contraction of pancreatic cancer in a subject, the determination of prognostication of pancreatic cancer in a subject and the determination of the presence/absence of recurrence of pancreatic cancer in a subject.

Further, the marker of the embodiment can be also used for the selection of the type of therapeutic method or the type of drug to apply to a subject. Here, the therapeutic method or drug is for the treatment of pancreatic cancer.

Further, the marker of the embodiment can be also used for the detection of pancreatic cancer cells in a sample.

(Kit)

According to the embodiment, a kit for the detection of pancreatic cancer is provided.

The kit comprises at least one kind of nucleic acid selected from a group consisting of a primer set (to be referred to as "the first primer set" hereinafter) to amplify hsa-miR-122-5p, an RT primer to reverse-transcribe hsa-miR-122-5p, an EL primer to elongate hsa-miR-122-5p and nucleic acid probes to detect hsa-miR-122-5p.

For example, the first primer set is LAMP primer set. For example, as the first primer set, at least one of the LAMP primer sets A and B listed in Table 2 can be used.

When the kit of the embodiment includes an RT primer and an EL primer, at least one of the reverse transcription and elongation primer sets A and B listed in Table 1 can be used.

The nucleic acid probe may include at least a part of sequence of hsa-miR-122-5p or a complementary sequence thereof, or at least a part of sequence of cDNA of hsa-miR-122-5p or a complementary sequence thereof.

The nucleic acids contained in the kit may be individually separated or combined in any combination, and contained in a container together with an appropriate carrier. The appropriate carrier is, for example, water or a buffer solution or the like. The container is, for example, a tube or a microtiter plate or the like. Further, the nucleic acids may be attached or fixed to a solid phase such as a microfluidic chip or the like, to be provided.

The kit may include, in addition to the nucleic acids, a reagent used for the reverse transcription, elongation and/or amplification, an indicator used for the detection (for example, a fluorochrome such as SYBRGreen or EVAGreen, or to detect the current, a metal complex such as ruthenium hexamine or the like) and the like.

The kit for the pancreatic cancer detection of the embodiment can be used for, for example, the determination of the presence/absence of contraction of pancreatic cancer in a subject, the determination of prognostication of pancreatic cancer in a subject and the determination of the presence/absence of recurrence of pancreatic cancer in a subject, and the like. Further, the kit of the embodiment can be also used for the selection of the type of therapeutic method or the type of drug to apply to a subject. Here, the therapeutic method or drug is for treatment of pancreatic cancer. Or, the kit of the embodiment can be also used for the detection of pancreatic cancer cells in a sample.

According to the another embodiment, the kit for the detection of pancreatic cancer is provided as a diagnostic composition or diagnostic medicine for pancreatic cancer, which contains at least one type of nucleic acid selected from a group consisting of a primer set to amplify hsa-miR-122-5p, an RT primer to reverse-transcribing hsa-miR-122-5p, an EL primer to elongate hsa-miR-122-5p and nucleic acid probes to detect hsa-miR-122-5p. Further, according to the embodiment, the use of at least one type of the nucleic acids in the production of the diagnostic composition for pancreatic cancer or the diagnostic medicine for pancreatic cancer is also provided.

Second Embodiment

In the second embodiment, as shown in FIG. 5, part (a), an analytical method for assisting the determination of the presence/absence of contraction of pancreatic cancer in a subject, which includes (a quantification step (S11)) quantifying hsa-miR-122-5p in a sample originated from the subject, is also provided.

Here, the "assisting the determination" includes, for example, acquiring information regarding the possibility that the subject is contracting pancreatic cancer. Such an analytical method includes the following steps as shown in FIG. 5, part (b).

(S11) a quantification step containing quantifying hsa-miR-122-5p in a sample originated from the subject; and (S12) an information acquisition step containing acquiring information regarding the possibility that the subject is contracting pancreatic cancer.

The quantification step (S11) can be carried out by a method similar to that of the quantification step (31). The information obtained in the information acquisition step (S12) is information regarding the amount of the target miRNA present in the sample, provided from the result of the quantification in the quantification step (S11). For example, the information is a quantification value of the amplification product or a quantification value of the target miRNA in a sample, or the like.

The information is compared with a control as described above or a predetermined threshold, to be used for the determination of the presence/absence of contraction of pancreatic cancer in a sample originated from a subject, the determination of prognostication of pancreatic cancer in a subject, the determination of the presence/absence of recurrence of pancreatic cancer, or the selection of the type of therapeutic method or the type of drug to apply to a subject, or the like.

EXAMPLES

Experiments carried out using the analytical methods or the kits of the embodiments will now be described.

Example 1. Quantification (the qRT-PCR Method) of Hsa-miR-122-5p in Serums of a Normal Person and Serums of Cancer Patients Serums prepared for the Examples were obtained from 16 samples of normal persons, 22 samples of breast cancer patients, 6 samples of colon cancer patients, 6 samples of stomach cancer patients, 3 samples of lung cancer patients, 6 samples of ovarian cancer patients, 11 samples of pancreatic cancer patients, 5 samples of bile duct cancer patient, 5 samples of esophagus cancer patients, 5 samples of liver cancer patients, 5 samples of brain tumor patients, 5 samples of bladder cancer patients, 5 samples of pancreatic cancer patients, 5 samples of sarcoma patients, 5 samples of endometrial cancer patients and 5 samples of uterus sarcoma patients.

From each serum, RNA was extracted. The extraction was carried out using NucleoSpin (registered trademark) miRNA Plasma (product name, a product of TAKARA BIO Corporation).

Then, short chain RNA present in each extracted sample was reverse-transcribed and thus cDNA was synthesized and amplified. The synthesis was done by using TaqMan (registered trademark) Advanced miRNA cDNA Synthesis Kit (product name, a product of ThermoFischer Scientific Company) according to the instruction book of TaqMan (registered trademark) Advanced miRNA Assay (a product name, a product of ThermoFischer Scientific Company).

Subsequently, TaqMan (registered trademark)-PCR was carried out to measure the Ct value and quantify the miRNA by using TaqMan (registered trademark) Fast Advanced Master Mix (a product name, a product of ThermoFischer Scientific Company) and TaqMan (registered trademark) Advanced miRNA Assay ID: 477855_mir. Here, $10^2$ copies were lower than or equal to the detection limit.

The results of the quantification are shown in FIG. 6. FIG. 6 is a box plat diagram showing the results of the quantification in the normal persons, cancer patients except for pancreatic cancer and pancreatic cancer patients.

More specifically, hsa-miR-122-5p was distributed in the order of $10^3$ to $10^4$ copies in the normal persons, in the order of $10^4$ to $10^5$ copies in the cancer patients except for pancreatic cancer, and in the order of $10^4$ to $10^6$ copies in the pancreatic cancer patients. The cancer patients were distributed over a higher value than that of the normal persons, and the pancreatic cancer patients showed a further higher value than those of the other cancers. These results indicate that a great amount of hsa-miR-122-5p present in the serum was observed in the pancreatic cancer patients.

The results of the quantification are shown in FIG. 6. FIG. 6 is a box plot diagram showing the results of the quantification in the normal persons, cancer patients except for pancreatic cancer and pancreatic cancer patients.

TABLE 3

| | AUC |
|---|---|
| Normal vs cancer | 0.95 |
| Pancreatic cancer vs Normal + other cancers | 0.85 |
| Pancreatic cancer vs other cancer | 0.83 |

The AUC which categorizes the normal persons and the cancer patients from each other was approximately 0.95, the AUC between the pancreatic cancer patients and the normal persons plus the cancer patients together was approximately 0.85, and the AUC between the pancreatic cancer patients and the other cancer patients was approximately 0.83.

Thus, it has been indicated that the miRNA of SEQ ID NO. 1, that is, hsa-miR-122-5p is a high-performance marker that detects pancreatic cancer while distinguishing from the normal persons and the other cancers.

Example 2. Quantification (the LAMP Method) of Hsa-miR-122-5p in Serum of Normal Persons and Serum of Cancer Patients The breakdowns of the samples are the same as those of Example 1. Further, the extraction of RNA was carried out by the same method as that of Example 1. 2 μL of each extracted sample was reverse-transcribed under conditions of 20 μL of reaction in volume, ten minutes at 16° C., five minutes at 42° C. and five minutes at 85° C. The composition of the reverse transcription reaction solution was 67 unit MultiScribe (registered trademark) Reverse Transcriptase (*), 1×RT Buffer (*), 0.1 mM of dNTPs (*), 4 U of RNaseOUT (product name, a product of ThermoFischer Scientific Company), and 10 nM of RT primer (Table 5, SEQ ID NO. 2). Those with a symbol "*" all included High-Capacity cDNA Reverse Transcription Kit (product name, a product of ThermoFischer Scientific Company).

To the reaction solution after the reverse transcription, 5 μL of an elongation liquid was added, and the elongation was carried out after two minutes at 95° C. and then by 20 times of a cycle of 20 seconds at 95° C.-30 seconds at 59° C.-10 seconds at 72° C. The elongation liquid was 25 μL of an elongation reaction solution containing DeepVent(exo-) DNApolymerase (0.5 U, a product of New England Bio), which was prepared to have a final concentration in each of 0.2×ThermoPol Buffer (with attachment of DeepVent(exo-) DNApolymerase), 0.2 mM of $MgSO_4$, 0.12 mM of dNTPs and 10 nM of EL primer (Table 5, SEQ ID NO. 3).

Then, 1 μL of the elongated product was LAMP-amplified under conditions of a reaction volume of 25 μL and 60 minutes at 65° C. and at the same time, the rise time of the fluorescence intensity was measured. The LAMP liquid contained 8 U of Tin(exo-)LF DNApolymerase (Optigene), and 0.5 μL of EvaGreen (registered trademark) (a product of Biotium), and was prepared to have a final concentration in each of 20 mM of Tris-HCl (pH 8.0), 50 mM of KCl, 8 mM of $MgSO_4$, 10 mM of $(NH_4)SO_4$, 0.1% of Tween-20, 0.8 M of betaine, 1.4 mM of each of dNTPs, 1.6 μM of an FIP primer (Table 5, SEQ ID NO. 6), 1.6 μM of a BIP primer (Table 5, SEQ ID NO. 7) and 0.8 μM of an LB primer (Table 5, SEQ ID NO. 8). With a real-time PCR device, the fluorescence intensity was measured over time, and a time period in which the level exceeds the threshold was measured.

TABLE 4

| Primer set A | | |
|---|---|---|
| Primer | SEQ ID NO | Sequence (5'-3' ) |
| RT | 2 | CGGAACGGCATAAAAAGCCCAAACACCA |
| EL | 3 | GAATGTGACCACGCGGATACAGACTTTCGATCCACGCTGGG ACCGAGGCCAGACTCTACCTGGGTGGAGTGTGACAA |
| FIP | 6 | CCAGCGTGGATCGAAAGTCTGTGAATGTGACCACGCGGAT |
| BIP | 7 | GACCGAGGCCAGACTCTACCTCGGAACGGCATAAAAAGCC |
| LB | 8 | GTGTGACAATGGTGTTTG |

The synthetic RNA of SEQ ID NO. 1 was reverse-transcribed, elongated and LAMP-amplified for each of the cases of 0, $10^2$, $10^3$, $10^4$ and $10^5$ copies/μL using the primer set A listed in Table 5, and similarly, the rise time of the fluorescence intensity was measured for each. From the results of these, an analytical curve of the number of copies of RNA of SEQ ID NO. 1 and the rise time was prepared for each (See FIG. 7). The analytical curve was excellent in indicating the miRNA concentration-dependency of the rise time of the turbidity. It has been thus made clear that the primer set A can specifically elongate and amplify the target miRNA. Using the analytical curve, the number of copies of RNA was calculated from the rise time in each sample.

The results of the quantification are shown in FIG. 8. FIG. 8 is a box plot diagram showing the results of the quantification in the normal persons, the cancer patients except for pancreatic cancer and the pancreatic cancer patients. The quantification value was distributed in the order of $10^4$ to $10^5$ copies in the normal persons, in the order of $10^5$ copies in the cancer patients except for pancreatic cancer, and in the order of $10^6$ copies in the pancreatic cancer patients. The cancer patients were distributed over a higher value than that of the normal persons, and the pancreatic cancer patients showed a further higher value than those of the other cancers. These results indicate that a great amount of hsa-miR-122-5p present in the serum was observed in the pancreatic cancer patients.

Area-under-curves (AUC) which respectively separate the normal persons and cancer patients, pancreatic cancer patients and normal persons plus patients with other cancers together, and pancreatic cancer patients and patients with other cancer into categories, respectively, are shown in Table 5 below.

TABLE 5

|  | AUC |
|---|---|
| Normal vs cancer | 0.85 |
| Pancreatic cancer vs Normal + other cancers | 0.83 |
| Pancreatic cancer vs other cancer | 0.80 |

The AUC which categorizes the normal persons and the cancer patients from each other was approximately 0.85, the AUC between the pancreatic cancer patients and the normal persons plus the cancer patients together was approximately 0.83, and the AUC between the pancreatic cancer patients and the other cancer patients was approximately 0.80.

Thus, it has been indicated that the miRNA of SEQ ID NO. 1, that is, hsa-miR-122-5p is a high-performance marker that detects pancreatic cancer while distinguishing from the normal persons and the other cancers. Further, the results of the example which employed the LAMP method, it has been made clear that a higher separation ability is achieved than in the case of qRT-PCR used in Example 1.

Example 3. Examination of LB Sequence

The elongation product for analytical curve, formed with the synthetic RNA, prepared in Example 2 was amplified by a method similar to that of Example 2 using an LB sequence of SEQ ID NO. 9 listed in Table 6 in place of the LB sequence of SEQ ID NO. 8.

TABLE 6

| Primer | SEQ ID NO | Sequence (5'-3') |
|---|---|---|
| LB | 9 | TGACAATGGTGTTTGGGC |

The results indicate that when using the LB primer of SEQ ID NO. 9 as well, the miRNA concentration-dependency of the rise time of the turbidity was excellent, and the nonspecific amplification obtained when the number of copies of miRNA was 0 was less. Therefore, it has been indicated the LB sequence of SEQ ID NO. 9 can also be used effectively in the LAMP system.

Example 4. Evaluation of Specificity of Primer Sets

Further, the synthetic RNA of SEQ ID NO. 1 was reverse-transcribed, elongated and LAMP-amplified for each of the cases of 0, $10^2$, $10^3$, $10^4$ and $10^5$ copies/μL using the primer set B listed in Table 7 under the same conditions as those of Example 2, and the rise time of the fluorescence intensity was measured for each.

TABLE 7

Primer set B

| Primer | SEQ ID NO | Sequence (5'-3') |
|---|---|---|
| RT | 4 | GGCGCCGAAACAATATTCCTCAAACACCA |
| EL | 5 | GATCTAGAAGGCCGCCAGTCGTTCAGCCTACGGCCGTTGTCATCCGTAG CAGGACGCTCAGGGTGGAGTGTGACAA |
| FIP | 10 | AACGGCCGTAGGCTGAACGGATCTAGAAGGCCGCCAGT |
| BIP | 11 | GTCATCCGTAGCAGGACGCTCAGGCGCCGAAACAATATTCCT |
| LB | 8 | GTGTGACAATGGTGTTTG |

The results are shown in FIG. 9. Even when using the primer set B, the miRNA concentration-dependency of the rise time of the turbidity was excellent. From these results, it has been made clear that the primer set B as well can specifically elongate and amplify the target miRNA. Therefore, it has been suggested that with use of the primer set, the accuracy of the detection of pancreatic cancer can be improved.

Example 5. Electrochemical Detection

A primer solution containing the FIP primer and BIP primer (48 μM each) used in Example 2, and an LB primer (24 μM) was prepared. 100 nL of the primer solution was spotted on a silicone-made flow path packing (width×height: 1 mm×1 mm) using a micro-dispenser. A DNA chip substrate (glass (0.8 mm)/titanium (500 nm)/gold (2,000 nm)) in which an electrode was patterned and the flow path packing were incorporated in a cassette, and thus a chip was manufactured.

Then, an LAMP reaction solution of the composition listed in Table 8 was prepared.

TABLE 8

Composition of LAMP reaction solution

| Ingredients | Final concentration |
|---|---|
| Tris-HCl (pH8.8) | 20 mM |
| KCl | 60 mM |
| $MgSO_4$ | 8 mM |
| $(NH_4)_2SO_4$ | 10 mM |
| Tween20 | 0.1% |
| dNTPs | 1.4 mM each |
| Tin exo-DNA polymerase | 48 units (x3) |
| Betaine | 0.8M |
| RuHex | 1 mM |
| Template | 1 μL |
| Amount of reaction solution | 60 μL |

1 μL of a template after the elongation used in Example 2 was added to the LAMP reaction solution, and electrochemical measurement was carried out under conditions indicated in Table 9.

TABLE 9

Conditions for electrochemical measurement

| Items | Details |
|---|---|
| Measurement method | Linear Sweep Voltammetry (LSV) |
| Sweep potential | 0.1 to −0.4 V |

17

18

TABLE 9-continued

Conditions for electrochemical measurement

| Items | Details |
| --- | --- |
| Sweep rate | 0.5 V/s |
| Temperature | 65° C. |

When the LAMP reaction was started, the reduction current value of ruthenium hexaamine (RuHex) began to increase. It is clear that the time at which the current increased was earlier as the amount of the elongation product present was greater, and therefore with use of the chip, the quantification can be detected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for differentially detecting pancreatic cancer in a subject who has a cancer comprising:

quantifying an amount of hsa-miR-122-5p in a sample from the subject and comparing the amount of hsa-miR-122-5p in the sample to an amount of hsa-miR-122-5p in non-pancreatic cancer individuals having breast cancer, colon cancer, lung cancer, ovarian cancer, prostate cancer, bile duct cancer, esophagus cancer, liver cancer, brain tumor, bladder cancer, sarcoma, endometrial cancer or uterus sarcoma; and detecting pancreatic cancer where the quantified amount of hsa-miR-122-5p in the sample exceeds the amount of hsa-miR-122-5p in the non-pancreatic cancer individuals;

wherein quantifying the amount of hsa-miR-122-5p in the sample from the subject is carried out using a primer set; and wherein the primer set contains:

an FIP primer comprising SEQ ID NO. 6, a BIP primer comprising SEQ ID NO. 7, an LB primer comprising SEQ ID NO. 8, the reverse transcription primer comprising SEQ ID NO. 2, and the elongation primer comprising SEQ ID NO. 3, an FIP primer comprising SEQ ID NO. 6, a BIP primer comprising SEQ ID NO. 7, an LB primer comprising SEQ ID NO. 9, the reverse transcription primer comprises SEQ ID NO. 2, and the elongation primer comprising SEQ ID NO. 3, or an FIP primer comprising SEQ ID NO. 10, a BIP primer comprising SEQ ID NO. 11, an LB primer comprising SEQ ID NO. 8, the reverse transcription primer comprising SEQ ID NO. 4, and the elongation primer comprising SEQ ID NO. 5.

2. The method of claim 1, wherein detecting pancreatic cancer is carried out without using a result of detection or quantification of a marker other than hsa-miR-122-5p.

3. The method of claim 1, wherein detecting pancreatic cancer comprises detecting prognostication of the pancreatic cancer in the subject or recurrence of the pancreatic cancer in the subject.

4. The method of claim 1, wherein the sample is serum.

5. The method of claim 1, wherein quantifying the amount of hsa-miR-122-5p in the sample from the subject comprises:

hybridizing a first primer portion included in a reverse-transcription primer and a sequence of hsa-miR-122-5p, wherein the first primer portion is hybridizable with the sequence of hsa-miR-122-5p, and the reverse-transcription primer further contains a first LAMP recognition sequence, reverse-transcribing the sequence of hsa-miR-122-5p, obtaining a reverse transcription product containing a complementary DNA of sequence of hsa-miR-122-5p, dissociating the reverse transcription product and the hsa-miR-122-5p from each other;

hybridizing a second primer portion included at 3' side end of an elongation primer and the complementary DNA of sequence of hsa-miR-122-5p included at 3' side end of the reverse transcription product, wherein the second primer portion is hybridizable with the complementary DNA of sequence of hsa-miR-122-5p, and the elongation primer further contains a second LAMP recognition sequence, elongating the elongation primer and the reverse transcription product as templates with respect to each other, obtaining an elongation product containing the sequence of hsa-miR-122-5p;

amplifying the elongation product using a primer set to amplify hsa-miR-122-5p by a LAMP reaction, thus obtaining an amplification product; and detecting the amplification product.

6. A kit for detecting pancreatic cancer rather than other cancers according to the method of claim 1, containing a primer set to amplify hsa-miR-122-5p, a reverse transcription primer to reverse-transcribe hsa-miR-122-5p, an elongation primer to elongate hsa-miR-122-5p, and at least one type of nucleic acid selected from a group comprising nucleic acid probes to detect hsa-miR-122-5p, said other cancers are breast cancer, colon cancer, lung cancer, ovarian cancer, prostate cancer, bile duct cancer, esophagus cancer, liver cancer, brain tumor, bladder cancer, sarcoma, endometrial cancer and/or uterus sarcoma;

wherein the primer set contains:

an FIP primer comprising SEQ ID NO. 6, a BIP primer comprising SEQ ID NO. 7, an LB primer comprising SEQ ID NO. 8, the reverse transcription primer comprising SEQ ID NO. 2, and the elongation primer comprising SEQ ID NO. 3, an FIP primer comprising SEQ ID NO. 6, a BIP primer comprising SEQ ID NO. 7, an LB primer comprising SEQ ID NO. 9, the reverse transcription primer comprises SEQ ID NO. 2, and the elongation primer comprising SEQ ID NO. 3, or an FIP primer comprising SEQ ID NO. 10, a BIP primer comprising SEQ ID NO. 11, an LB primer comprising SEQ ID NO. 8, the reverse transcription primer comprising SEQ ID NO. 4, and the elongation primer comprising SEQ ID NO. 5.

7. The method of claim 1, further comprising providing or producing data obtained by detecting the pancreatic cancer for diagnosis and treatment of the pancreatic cancer.

8. The method of claim 1, wherein further comprising:

obtaining the sample from the subject, and pretreating the sample from the subject to put a body fluid, which is contained in the sample from the subject, in a suitable form for amplification of hsa-miR-122-5p, wherein the pretreating is to centrifuge, deposit, extract and/or separate the sample from the subject, and the quantifying is to quantify the amount of hsa-miR-122-5p in the body fluid.

* * * * *